United States Patent [19]
Ikenaga et al.

[11] Patent Number: 4,961,431
[45] Date of Patent: Oct. 9, 1990

[54] TOILET DEVICE WITH HEALTH EXAMINATION SYSTEM

[75] Inventors: Takao Ikenaga; Toshifumi Shigematsu; Akio Kusumoto; Kimiyoshi Yamamoto, all of Kanagawa; Masatoshi Yada, Fukuoka, all of Japan

[73] Assignee: Toto, Ltd., Fukuoka, Japan

[21] Appl. No.: 149,190

[22] Filed: Jan. 27, 1988

[30] Foreign Application Priority Data

| Jan. 27, 1987 | [JP] | Japan | 62-16392 |
| Jan. 27, 1987 | [JP] | Japan | 62-16393 |
| Jan. 27, 1987 | [JP] | Japan | 62-10516[U] |
| Jan. 27, 1987 | [JP] | Japan | 62-10515[U] |
| Jan. 27, 1987 | [JP] | Japan | 62-10514[U] |
| Jan. 27, 1987 | [JP] | Japan | 62-10513[U] |
| Jan. 30, 1987 | [JP] | Japan | 62-20217 |
| Jan. 30, 1987 | [JP] | Japan | 62-20216 |
| Jan. 30, 1987 | [JP] | Japan | 62-20215 |
| Jan. 30, 1987 | [JP] | Japan | 62-12528[U] |
| Jan. 30, 1987 | [JP] | Japan | 62-12529[U] |
| Jan. 30, 1987 | [JP] | Japan | 62-12530[U] |

[51] Int. Cl.$^5$ .................................................. A61B 5/00
[52] U.S. Cl. ..................................... 128/760; 128/771
[58] Field of Search .............. 128/760, 771; 4/420; 73/864.21, 864.81–864.85

[56] References Cited

U.S. PATENT DOCUMENTS

| 4,466,445 | 8/1984 | Abrams | 128/736 |
| 4,524,777 | 6/1987 | Kisioka et al. | 128/677 |
| 4,544,687 | 11/1985 | Carter et al. | 128/771 |

FOREIGN PATENT DOCUMENTS 59-183969 12/1984 Japan .

OTHER PUBLICATIONS

Patent Abstracts of Japan, vol. 9, No. 269 (P-400) (1015), 24 Jul. 1985 and JP-A-60 117 157 (Toshiba K.K.).
Patent Abstracts of Japan, vol. 6, No. 137 (P-130) (1015), 24 Jul. 1982; and JP-A-57 59 168 (Kimura Giken K.K.) 09-04-1982.

Primary Examiner—Max Hindenburg
Attorney, Agent, or Firm—Lowe, Price, LeBlanc, Becker & Shur

[57] ABSTRACT

A toilet device with a health examination system, includes a urine sampler for sampling a portion of urine from a urine receiver, a urine analyzer for measuring the proportion of a particular constituent of the urine, a measuring unit for measuring at least one of the blood pressure, heart rate, and temperature of a user of the urine receiver, and a display unit for displaying the results of measurement by the urine sampler, the urine analyzer, and the measuring unit.

39 Claims, 12 Drawing Sheets

FIG. 3
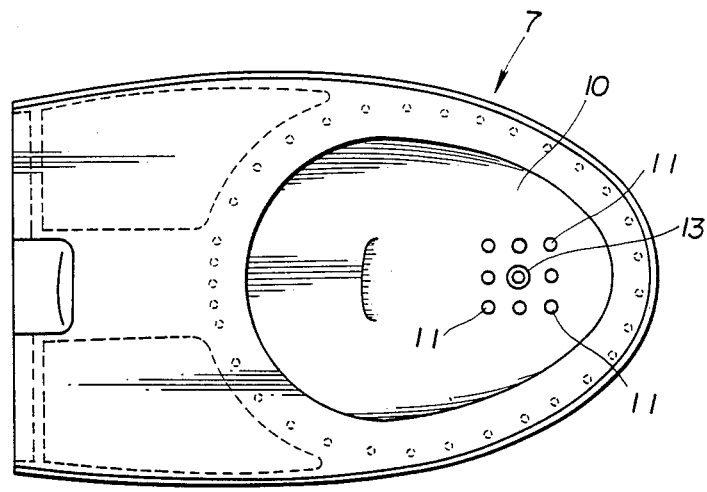
FIG. 5
FIG. 4
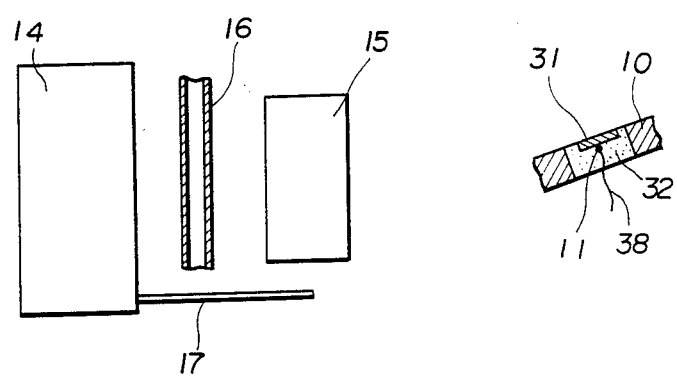

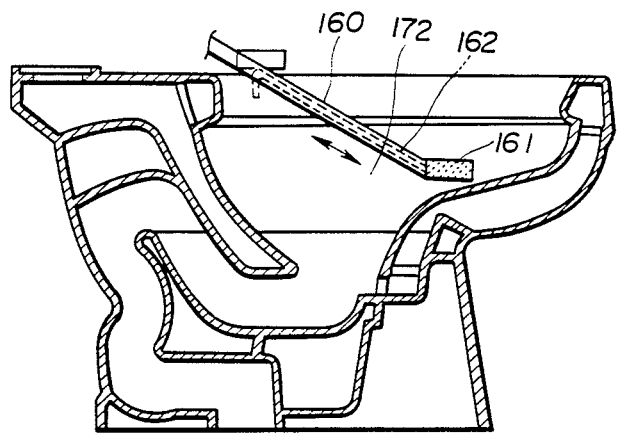
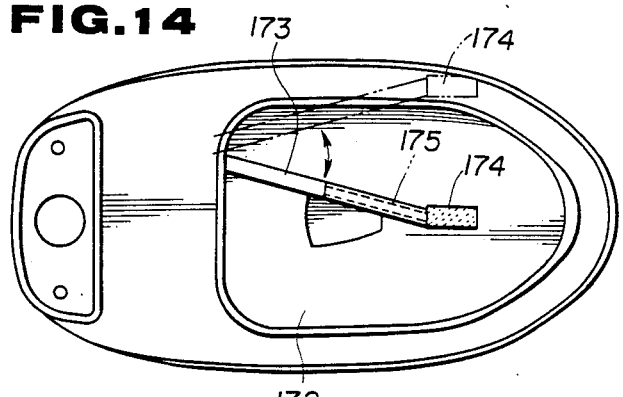
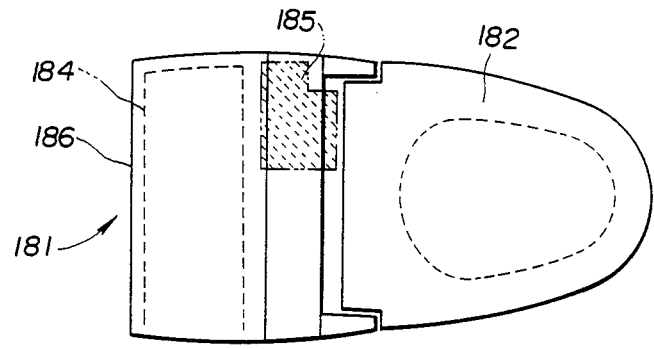

4,961,431

TOILET DEVICE WITH HEALTH EXAMINATION SYSTEM

BACKGROUND OF THE INVENTION

1. Field of the Invention

The present invention relates to a toilet device including a toilet and a measurement system for checking the health of the toilet user for a variety of examination items.

2. Description of the Relevant Art

There are known measurement or examination systems for sampling a portion of urine excreted by the user of a toilet, and analyzing the sampled urine with various analyzers to measure the amounts of glucose, albumin, and other substances contained in the urine. Examines of such systems are disclosed in Japanese Laid-Open Patent Publications Nos. 57-59168, 59-217844, 60-117157, and 60-155977, and Japanese Laid-Open Utility Model Publication No. 59-183969, for example.

However, analysis of urine only is not sufficient as exhaustive examination items for checking the health of the toilet user on an everyday basis for the discovery and prevention of an adult disease or diseases.

SUMMARY OF THE INVENTION

According to the present invention, there is provided a toilet device with a health examination system, comprising a urine receiver, first measuring means for sampling a portion of urine from the urine receiver and measuring the proportion of a particular constituent of the urine, second measuring means for measuring at least one of the blood pressure, heart rate, and temperature of a user of the urine receiver, and display means for displaying the results of measurement by the first and second measuring means.

It is therefore an object of the present invention to provide a toilet device capable of checking the health condition of a user more thoroughly than heretofore by obtaining not only data on urine but also data on at least one of the blood pressure, heart rate, and temperature of the user.

Another object of the present invention is to provide a toilet device which have measuring means that are less subject to malfunctions or failures.

The above and further objects, details and advantages of the present invention will become apparent from the following detailed description of preferred embodiments thereof, when read in conjunction with the accompanying drawings.

BRIEF DESCRIPTION OF THE DRAWINGS

FIG. 3 is a plan view of the bowl shown in FIG. 2;

FIG. 4 is an enlarged fragmentary cross-sectional view of a urine temperature sensor;

FIG. 5 is a schematic view of a urine analyzer;

FIG. 13 is a vertical cross-sectional view of a bowl, showing another urine sampler;

FIG. 14 is a plan view of a bowl, showing still another urine sampler;

FIG. 16 is a plan view of the bowl shown in FIG. 15;

DETAILED DESCRIPTION OF THE PREFERRED EMBODIMENTS

Figure 1:
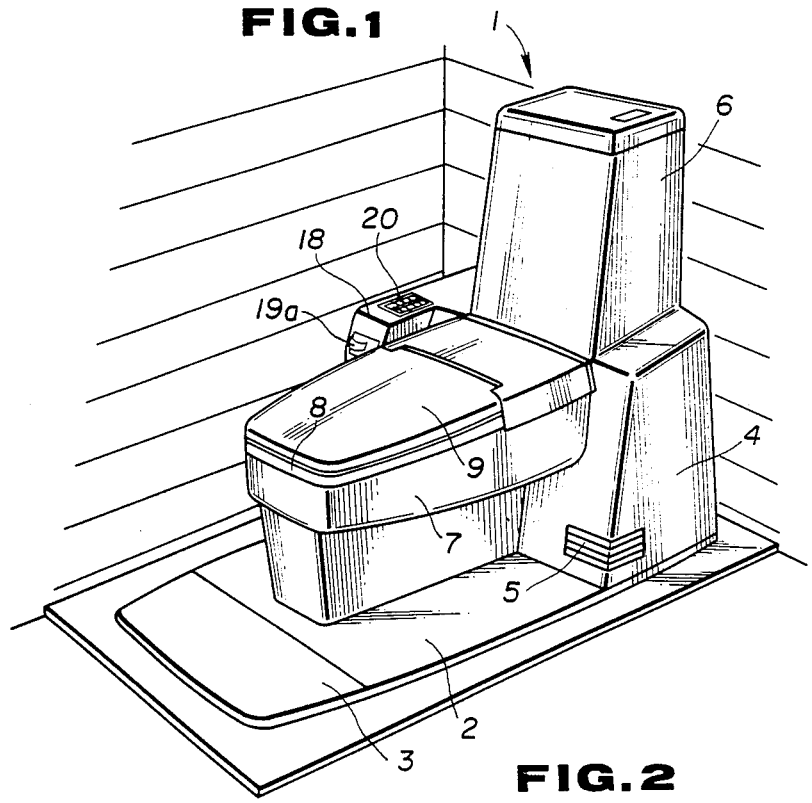
FIG. 1 is a perspective view of a toilet device according to an embodiment of the present invention.

As shown in FIG. 1, a toilet device 1 has a bottom plate 2 incorporating a scales 3 in its front portion. The bottom plate 2 supports on its near portion a box 4 containing an air discharge fan and a pipe, the box 4 having a suction window 5 defined in a portion thereof for drawing air which will be discharged by the air discharge fan. A water tank 6 is disposed on the box 4 for storing flushing water. A urine receiver or bowl 7 extends forwardly from the box 4 and is disposed on the bottom plate 2.

Figure 2:
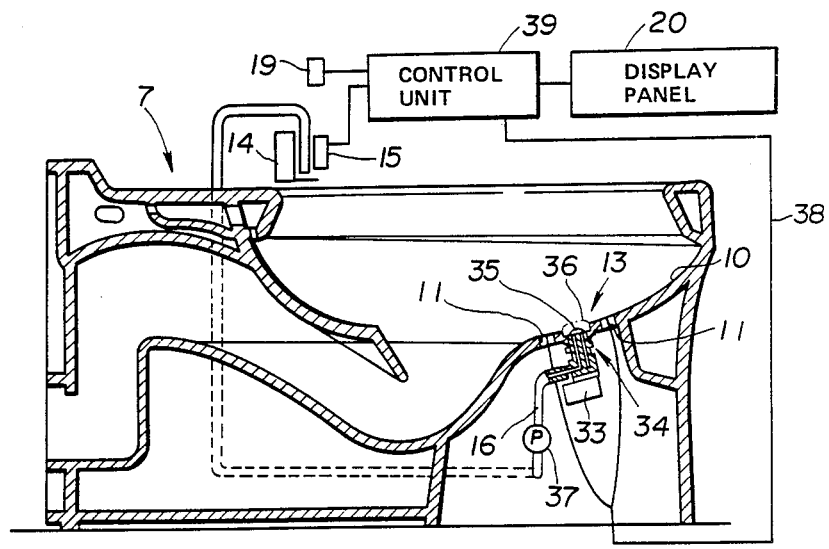
FIG. 2 is a vertical cross-sectional view of a bowl with a urine sampler and urine temperature sensors, with associated units shown in block form.

A seat 8 and a seat lid 9 are pivotally mounted on the bowl 7. As shown in FIG. 2, the bowl 7 has an inner bowl surface or urine receiving surface 10 with a plurality of temperature sensors 11 embedded therein at an area to which excreted urine will directly be applied. The excreted urine can therefore be applied directly to any of these temperature sensors 11, so that the temperature of the urine can be measured before it is lowered. The highest one of the temperatures measured by the respective temperature sensors 11 is adopted as a temperature closest to the body temperature of the user of the toilet device 1. Therefore, the detected temperature data is highly reliably used as the body temperature.

As shown in FIG. 3, a total of eight temperature sensors 11 are embedded around a urine sampler 13 (described later) according to the illustrated embodiment. As illustrated in FIG. 4, each of the temperature sensors 11 has an upper surface covered with a protective layer 31 made of a good thermal conductor such as metal. The protective layer 31 and the temperature sensor 11 are embedded in a filler 32 of resin which is made of a poor thermal conductor. The filler 32 has an outer surface which lies flush with the outer surfaces of the protective layer 31 and the inner bowl surface 10, thus providing a smooth surface over the temperature sensors 11. Therefore, any excreted urine or dirt will not remain attached to the upper surface area of the temperature sensors 11, and the upper surface area of the temperature sensors 11 can easily be cleaned.

The urine sampler 13 comprises an on-off valve 34 (FIG. 2) which can be opened and closed by a motor 33. The on-off valve 34 has a valve body 35 over which a strainer 36 is disposed for preventing foreign matter such as dirt from entering a conduit 16 connected to the on-off valve 34. As shown in FIG. 5, a test paper cassette 14 and a photoelectric sensor 15 are positioned above a rear portion of the bowl 7. The urine extracted by the urine sampler 13 is fed through the conduit 16 by a pump 37 so as to drop onto a piece of test paper 17 discharged from the test paper cassette 14. The degree of coloration of the piece of test paper 17 is detected by the photoelectric sensor 15 comprising a photodiode or the like for measuring the amounts of glucose or sugar, albumin, urobilin, and occult blood which are contained in the urine. The piece of test paper 17 is discarded into the bowl 7 after the detecting process.

The urine may be sampled by any of various other arrangements. For example, as described later on, a urine sampler may be mounted on the distal end of a pipe which is swingable laterally or movable back and forth in the bowl 7, and a portion of the excreted urine may be sampled by such a urine sampler under suction.

As described later on, the conduit 16 is cleaned by a cleanser periodically or at any desired time so that no scale will be deposited in the conduit 16.

A block 18 is integrally formed with and extends forwardly from a righthand portion of the box 4. A unit 19 for measuring the blood pressure and heart rate of the user is disposed on the front face of the block 18.

The measuring unit 19 is in the form of a band 19a for insertion of a finger of the user therethrough, the band 19a comprising a tube into which air can be supplied. When a finger of the user is inserted through the band 19a, air is supplied into the tubular band 19a for forcibly pressing the finger to temporarily interrupt the blood flow in the finger. Then, the supplied air is gradually discharged. The blood pressure at the time the blood starts to flow again is detected as a highest blood pressure by the band 19a. The blood pressure at the time the air is completely removed and the blood flow returns to the normal state is detected as ta lowest blood pressure by the band 19a. The heart rate is measured by a heartbeat sensor through the band 19a.

The data items measured by the temperature sensor 11, the photoelectric sensor 15, and the measuring unit 19 are delivered over lead wires 38 and stored in a memory in a control unit 39. The stored data items are displayed on a display panel 10 on the upper surface of the block 18. The urine temperature to be displayed as the body temperature may be compensated for any temperature drop which may have been be caused before the excreted urine reaches the temperature sensors 11.

Figure 6:
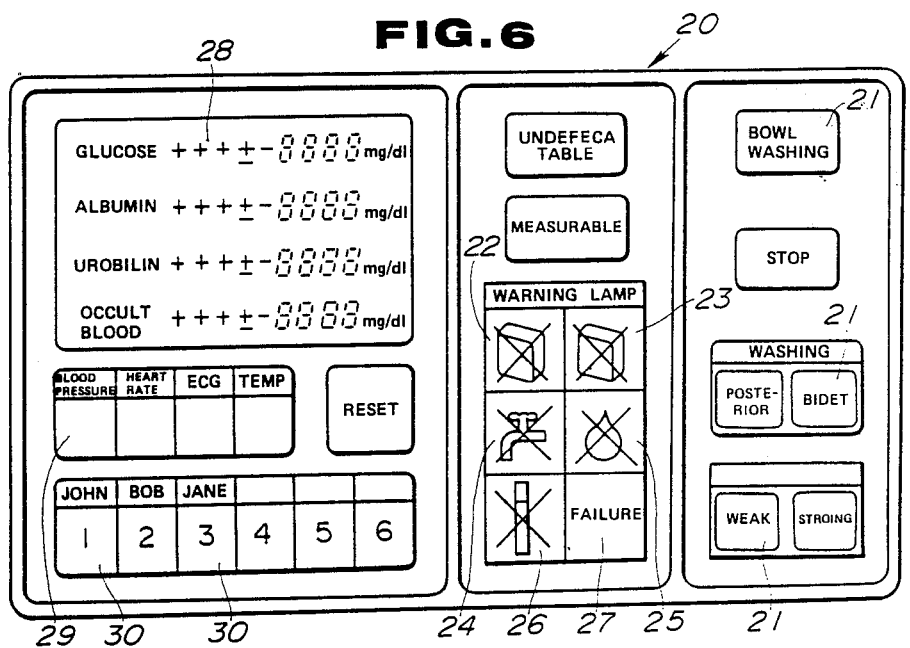
FIG. 6 is an enlarged plan view of a display panel.

The display panel 20 will be described by way of example with reference to FIG. 6.

The display panel 20 is divided into three areas. The righthand area, as shown, has a bowl washing button 21 and body parts washing buttons 21. The central area has various warning lamps. The lefthand area has various data indicators. More specifically, the warning lamps in the central area include a lamp 22 for indicating that no test paper cassette is set in place, a lamp 23 for indicating that the toilet device is running short of a cleanser, a lamp 24 for indicating a water supply failure, a lamp 25 for indicating insufficiency of urine to be examined, a lamp 26 for indicating that no test paper is set, and a lamp 27 for indicating other failure. The indicators in the display area include an indicator 28 for indicating various urine data items, and an indicator 29 for indicating the blood pressure, the heart rate, and other data items. The righthand area also includes registered-user buttons 30. When one of the registered-user buttons 30 is pressed, the measured data items are displayed on a graphic display or printed as a graph by a printer or the like on a time-dependent basis, and/or transmitted to a data storage center linked to a medical organization so that the registered user who has pushed the corresponding registered-user button 30 can be identified for centralized health care provided by the medical organization.

Figure 7:
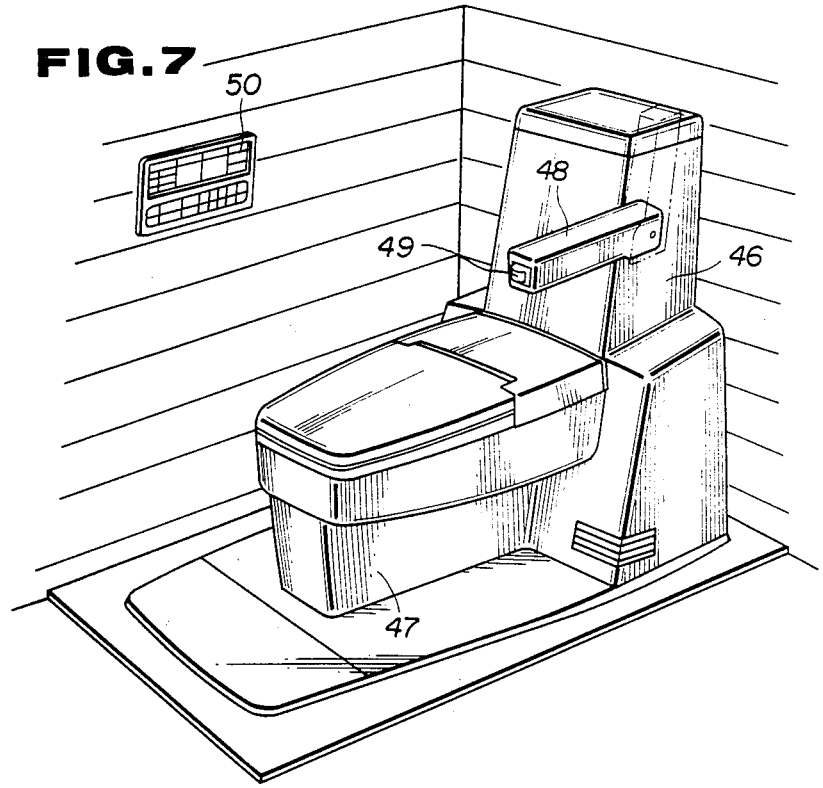
FIG. 7 is a perspective view of a toilet device according to another embodiment of the present invention.

FIG. 7 shows a modified toilet device according to the present invention. A swingable arm 48 is attached to a lefthand surface of a water tank 46, and a measuring unit 49 for measuring the blood pressure, heart rate, and electrocardiographic condition of the user is mounted on the distal end of the swingable arm 48. It is preferable that the swingable arm 48 as it swings forwardly to its horizontal position be vertically positioned substantially at the height of the heart of the toilet user sitting on the toilet seat on a toilet bowl 47. A display panel 50 is attached to a wall of the bathroom.

Figure 8:
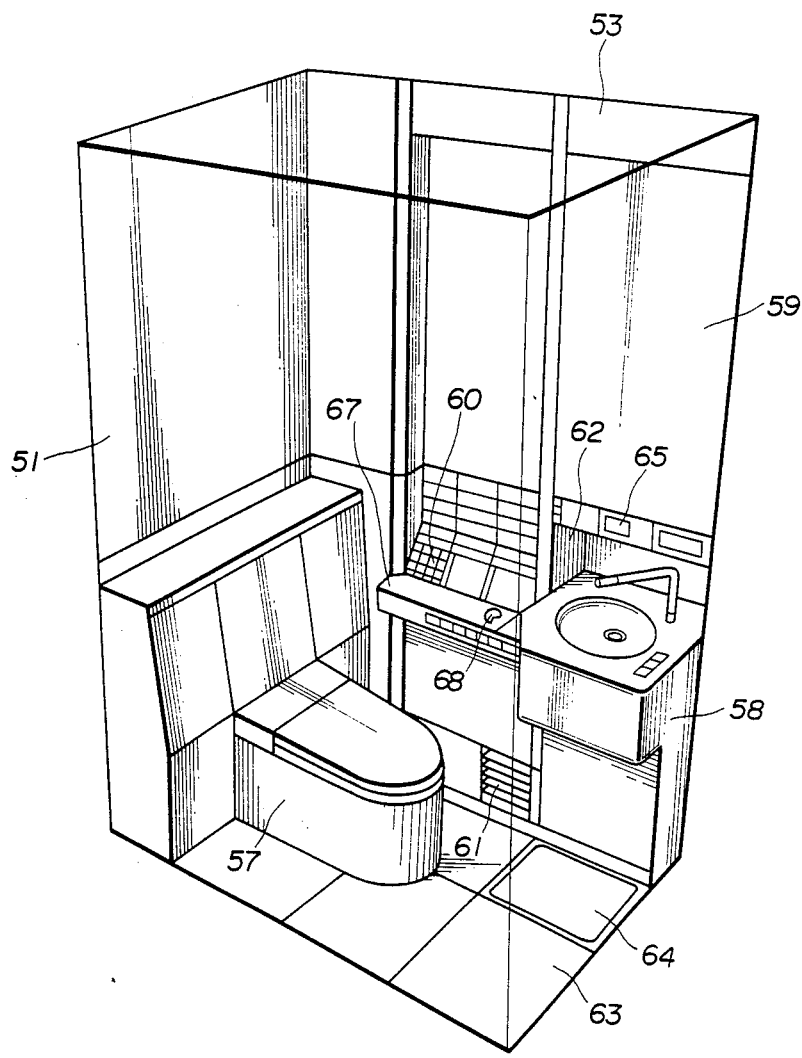
FIG. 8 is a perspective view of a toilet device according to still another embodiment of the present invention.

FIG. 8 illustrates a toilet device according to a further modification of the present invention. The toilet device includes a bowl 57 projecting forwardly from a wall 51. A sink 58, a mirror 59, display panels 60, and a ventilation window 61 are installed on another wall 53 normal to the wall 51. A partition 62 is disposed between the display panels 60 and the sink 58 for preventing water droplets from being applied from the sink 58 to the display panels 60. A scales 64 is embedded in a floor 63 below the sink 58. The weight of the toilet user can automatically be measured by the scales 64 when the user stands on the scales 64 to wash the hands after excretion. The measured weight is displayed on a display unit 65 on the lower edge of the mirror 59.

A table 67 projects from the lower edges of the display panels 60 toward the bowl 57 at a height substantially equal to the height of the heart of the user sitting on the bowl 57, so that the lefthand arm of the user will be naturally placed on the table 67. The table 67 supports thereon a measuring unit 68 for measuring the blood pressure and the heart rate of the user, the measuring unit 68 being identical to the measuring unit 19 described above.

The toilet device of the above embodiment is capable of examining, on an everyday basis, the toilet user for various items required to be checked for health care. Since the toilet user can be examined simply by depressing buttons without requiring any special complex process, the toilet device can easily be used by elderly people or other handicapped persons.

Figure 9:
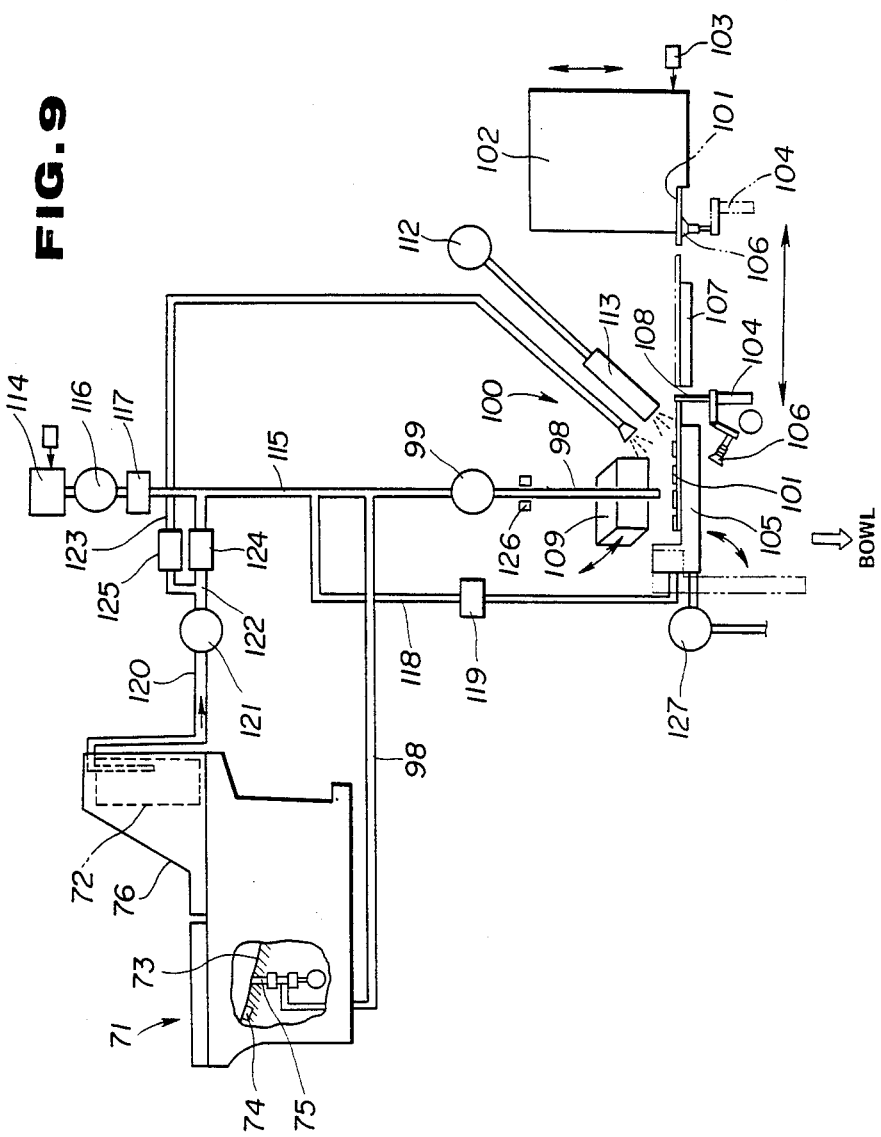
FIG. 9 is a view showing a piping arrangement of a toilet device of the invention, the view also showing a urine sampler and a urine analyzer.

FIG. 9 shows a piping arrangement and an urine analyzer for use with a toilet device of the present invention. A flushing water tank 72 accommodated in a housing 76 is mounted on an upper surface of a bowl 71. The bowl 71 has a urine receiving surface or bowl surface 73 in which there are embedded a temperature sensor 74 and a pop-up urine sampler on-off valve 75.

Figure 10:
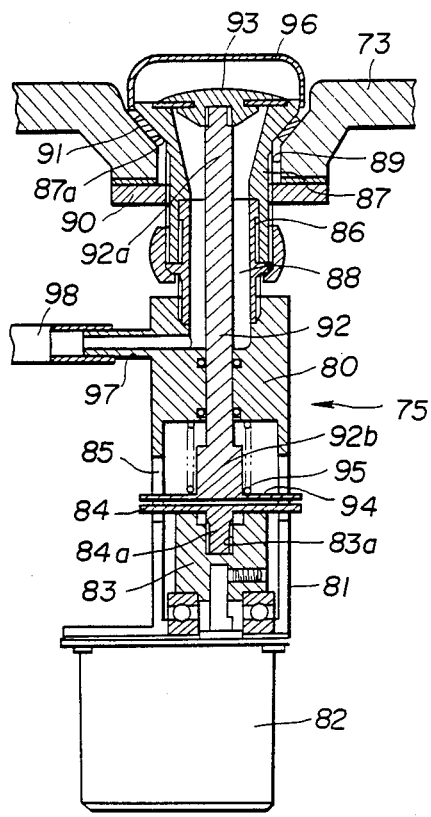
FIG. 10 is an enlarged cross-sectional view of an on-off valve of a urine sampler, mounted in a bowl surface of a bowl.

As shown in FIG. 10, the on-off valve 75 is of basically the same structure as that of the on-off valve 34 shown in FIG. 2. The on-off valve 75 has a valve case 80 including a lower tubular portion 81 having a lower end to which is reversible motor 82 is fixed. The motor 82 has its output shaft connected to a rotor 83 disposed in the tubular portion 81, the rotor 83 having a central recess 83a in which a support shaft 84a of a vertically movable body 84 is threaded. The vertically movable body 84 has a portion engaging in vertical slits 85 defined in the tubular portion 81 for preventing the vertically movable body 84 from being rotated about its vertical axis. When the motor 82 is rotated, the vertically movable body 84 is vertically moved along the slits 85 since the body 84 is threaded in the rotor 83.

A valve seat 87 is coupled to the upper surface of the valve case 80 through a threaded joint 86. The joint 86 and the valve seat 87 are tubular in shape and have urine passages 88 defined vertically therethrough. The valve seat 87 has a tapered conical outer peripheral surface 87a which is firmly pressed against a complementarily tapered conical surface of a hole 89 defined in the bowl surface 73 through a seal member by tightening a nut 90 to secure the valve seat 87 to the bowl surface 73.

A rod 92 extending through the valve case 80 is disposed in the urine passage 88. The rod 92 has a distal upper end 92a on which a valve body 93 for opening and closing the urine passage 88 is mounted. The rod 92 also has on its lower end 92b facing the tubular portion 81 a flange 94 confronting the vertically movable body 84. A spring 95 is disposed under compression between the flange 94 and an inner surface of the valve case 80 for normally urging the rod 92 downwardly in a direction to enable the valve body 93 to close the urine passage 88.

The upper surface of the valve seat 87 is covered with a cap-shaped strainer 96 for preventing foreign matter from entering the urine passage 88 when the valve body 93 is moved upwardly to open the urine passage 88.

The valve case 80 has a joint pipe 97 projecting laterally therefrom and communicating with the urine passage 88, the joint pipe 97 being coupled to one end of a conduit 98. As shown in FIG. 9, the conduit 98 has a urine sampling pump 99 for drawing sampled urine into a urine analyzer 100. The urine analyzer 100 is actually positioned within the housing 76 rearwardly and upwardly of the bowl surface 73 of the bowl 71.

Figure 11:
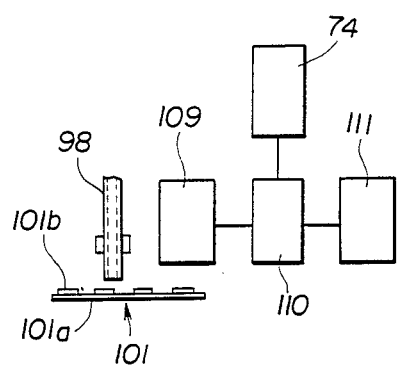
FIG. 11 is a view of a urine analyzer different from that of FIG. 5, the urine analyzer being connected to a control unit, a display unit, and a urine temperature sensor.

The analyzer 100 has a cassette 102 containing many pieces of test paper 101, the cassette 102 being vertically movable by a motor. The remaining pieces of test paper 101 in the cassette 102 can be detected by a sensor 103. As shown in FIG. 11, each of the test paper pieces 101 comprises a resin sheet 101a and a plurality of test pads 101b attached thereto. The test pads 101b can produce color by contact with different constituents of the urine, such as glucose, albumin, urobilin, and occult blood, for example.

The pieces of test paper 101 in the cassette 102 are delivered, one at a time, onto a rack 105 disposed directly below the opening in the lower end of the conduit 98 by means of a movable cylinder unit 104. The cylinder unit 102 is movable horizontally by a motor (not shown) and has a suction cup 106 for attracting the lower surface of a lowermost test paper piece 101 in the cassette 102. With the suction cup 106 attracting the lowermost test paper piece 101, the cylinder unit 104 is moved away from the cassette 102 to pull the test paper piece 101 out of the cassette 102 onto a guide plate 107. Then, a rod 108 of the cylinder unit 104 is projected, and the cylinder unit 104 is moved to enable the rod 108 to push the trailing end of the test paper piece 101 onto the rack 105. The rack 105 is swingable downwardly in order to dischard the test paper piece for after the urine has been tested.

A urine data sensor 109 is disposed near the rack 105 and movable toward and away from the rack 105. Data values detected by the urine data sensor 109 are supplied to a control unit 109 (FIG. 11) which processes the applied data items and displays them on a display unit 111. The display unit 111 is mounted on a bathroom wall, a water tank side wall, or the like for displaying not only the data items detected by the sensor 109 but also the temperature detected by a temperature sensor 74 identical to the temperature sensors 11 (FIG. 2).

A heater 113 is disposed in the vicinity of the rack 105 for draining air from a blower 112 and applying the dried air to the upper surface of the rack 105.

To the conduit 9, there is connected a pipe 115 from a cleanser tank 114 having a pump 116 and a valve 117. A pipe 118 is branched from the pipe 115 and has a valve 119, the pipe 118 having a distal end facing a portion of the rack 105.

A pipe 120 having a pump 121 leads from the flushing water tank 72 and is branched into pipes 122, 123 downstream of the pump 121. The pipe 122 is connected through a valve 124 to the pipe 125. The pipe 123 has a valve 125 and has a lower end opening above the rack 105. An excessive urine suction pump 127 serves to discharge excessive urine from the rack 105.

When the user presses a start button and excretes urine, the motor 82 of the on-off valve 75 is energized to elevate the valve body 93 and the pump 99 is actuated to feed a portion of the excreted urine into the conduit 98. The urine thus introduced into the conduit 98 is detected by a passage sensor 126, whereupon a piece of test paper 101 is automatically delivered from the cassette 102 onto the rack 105, and the urine is allowed to drop on the test paper piece 101. The degree of coloration of the test paper piece 101, which is caused by the application of the urine; is detected by the urine data sensor 109 for a given period of time. The detected values and the temperature detected by the temperature sensor 74 are displayed on the display unit 111.

After the urine data items have been measured, the valves 119, 124, 125 are opened and the pumps 121, 99 are actuated to wash the interiors of the pipe 98 and the pump 99, and the upper surface of the rack 105. At this time, the flushing water is ejected from the on-off valve 75 over the bowl surface 93. However, the ejected water is prevented from being scattered out of the bowl 71 by the valve body 93 and the strainer 96. During the washing process, the rack 105 is turned downwardly to discard the urine, the flushing water, and the test paper piece 101 into the bowl 71.

Then, the pump 121 is inactivated, the valves 119, 124, 125 are closed, and the pump 99 is actuated to discharge remaining water from the urine passage 88 and the conduit 98 into the bowl 71. Thereafter, the valve body 93 is closed. The urine excreted by a next toilet user can thus be examined without being diluted by the flushing water.

Then, the rack 105 is swung upwardly in preparation for a next test cycle, and air from the blower 112 is passed through the heater 113 to the rack 105 for drying the upper surface thereof.

At periodic intervals, once a day, for example, or at any desired times, the valve 117 is opened and the pump 116 is driven to supply the cleanser from the cleanser tank 114 onto the conduit 98 and onto the rack 105 to decompose the remove urine scales.

In the above embodiments, urine is sampled through the on-off valve embedded in the urine receiving surface or bowl surface of the bowl or urine receiver. However, the present invention is not limited to the foregoing urine sampling structures. Urine sampling structures according to other embodiments will be described below.

Figure 12:
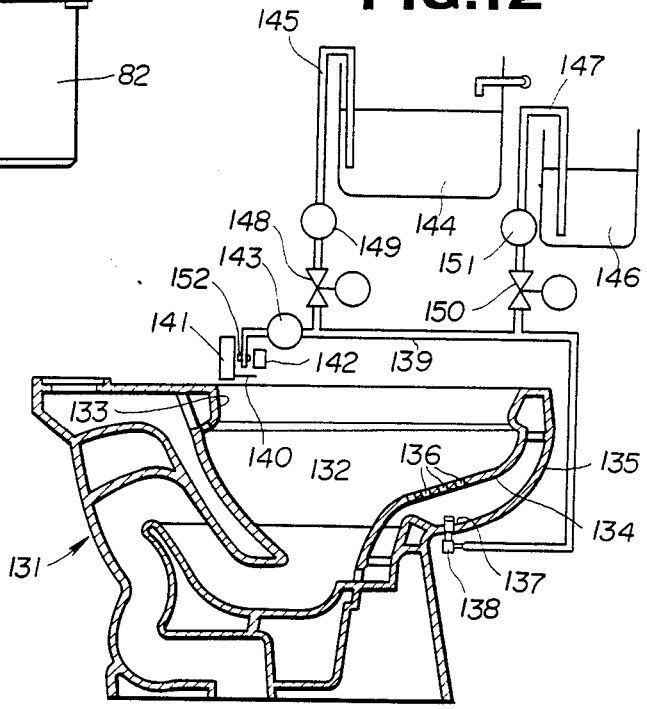
FIG. 12 is a vertical cross-sectional view of a bowl having a urine sampler different from that of FIG. 2, with a different piping arrangement from that of FIG. 9 being also shown.

FIG. 12 shows a bowl 131 having a double-walled bowl body 132 composed of an inner wall 134 and an outer wall 135. The inner wall 134 has a plurality of urine sampling holes 136 defined in a urine receiving surface 133 to which excreted urine is applied. The outer wall 135 has a downwardly concave urine sampler 137 below the urine sampling holes 136. The urine sampler 137 has a bottom in which a suction fitting 138 is mounted. The suction fitting 138 is connected to one end of a conduit 139, the other end of which is open as an outlet opening above a rear portion of the bowl 131.

An urine analyzer 155 is disposed near the open end of the conduit 139. The urine analyzer 155 is similar to that shown in FIG. 2, including a cassette 141 storing a plurality of pieces of test paper 140, a urine data sensor 142 comprising a photodiode, and a urine passage sensor 152 positioned on the conduit 139 in the vicinity of the outlet opening of the conduit 139. When the passage of urine dropped from the outlet opening of the conduit 139 is detected by the urine passage sensor 152, a piece of test paper 140 is fed forwardly from the cassette 141 to receive urine droplets thereon.

A pump 143 is disposed in the conduit 139 for drawing urine. A pipe 145 extending from a flushing water tank 144 and a pipe 147 extending from a cleanser tank 146 are connected to the conduit 139 upstream of the pump 153. The pipe 145 has a valve 148 and a pump 149, and the pipe 147 has a valve 150 and a pump 151.

When the toilet user turns on a start switch and excretes urine, the urine which drops through the urine sampling holes 136 in the inner wall 134 pools in the urine sampler 137. The urine is then delivered from the urine sampler 137 via the suction fitting 138 and the conduit 139 to the urine analyzer 155, and allowed to drop onto a test paper piece 140 which has automatically been pulled out of the cassette 141. The degree of coloration of the test paper piece 140 caused by contact with the urine droplets is detected by the sensor 142 for a given interval of time.

After urine constituents have been measured by the sensor 142, the test paper piece 140 is thrown away into the bowl 131. Thereafter, the valve 148 is opened and the pumps 149, 143 are actuated to introduce flushing water into the conduit 139 and the pump 143. In this embodiment, the displacement of the pump 149 is selected to be larger than the displacement of the pump 143. Therefore, the conduit 139 and the pump 143 can simultaneously be washed by simultaneously driving the pumps 143, 149. Alternatively, after the pump 143 has been washed by simultaneous operation of the pumps 143, 149, only the pump 149 may be actuated to wash the conduit 139. At this time, the suction fitting 138 remains open to discharge any urine from the urine sampler 137 into the trap in the bowl 31. The inner wall 134 has an upper wall portion 133 projecting inwardly for preventing the excreted urine and the flushing water from being scattered out of the bowl 131.

When the conduit 139 is filled with flushing water, the valve 148 is closed, the pump 149 is turned off, and then the pump 143 is actuated to discharge any water remaining in the conduit 139 and the urine sampler 137 in preparation for a next urine analyzing cycle.

Scales deposited in the conduit 139 cannot completely be removed by being washed by flushing water only. Therefore, the conduit 139 is washed by a cleanser at periodical intervals. More specifically, the valve 148 is closed, and the valve 150 is opened and the pump 151 is actuated. The pump 143 is also operated at the same time that or slightly after the pump 151 is operated, thereby to introduce the cleanser into the conduit 139 and the pump 143, for thus decomposing scales. Thereafter, the valve 150 is closed and the pump 151 is turned off to remove away the decomposed scales with the flushing water. Then, the flushing water is discharged in the same manner as described above in preparation for a next analyzing cycle.

FIGS. 13 and 14 show urine sampling structures according to further embodiments of the present invention. Urine analyzers for use with these urine sampling structures are omitted from illustration as they are identical to the urine analyzer of the preceding embodiment.

According to the embodiment shown in FIG. 13, a urine suction unit 161 is mounted on the distal end of a pipe 160 which is longitudinally movable from a position behind the buttocks of the toilet user seated on the seat toward a position below the buttocks of the user. Urine sampled by the urine suction unit 161 is delivered through a conduit 162 in the pipe 160 to the urine analyzer.

In the embodiment of FIG. 14, a urine suction unit 174 is mounted on the distal end of a pipe 173 that is swingable laterally in a bowl 172 about the opposite rear end of the pipe 173. Urine sampled by the urine suction unit 174 is fed via a conduit 175 in the pipe 173 to the urine analyzer.

In each of the embodiments shown in FIGS. 13 and 14, the urine analyzer including the test paper pieces and the photoelectric sensor and disposed above the rear portion of the bowl, and also the flushing water tank for storing flushing water to wash the bowl should preferably be covered with a cover.

Figure 15:
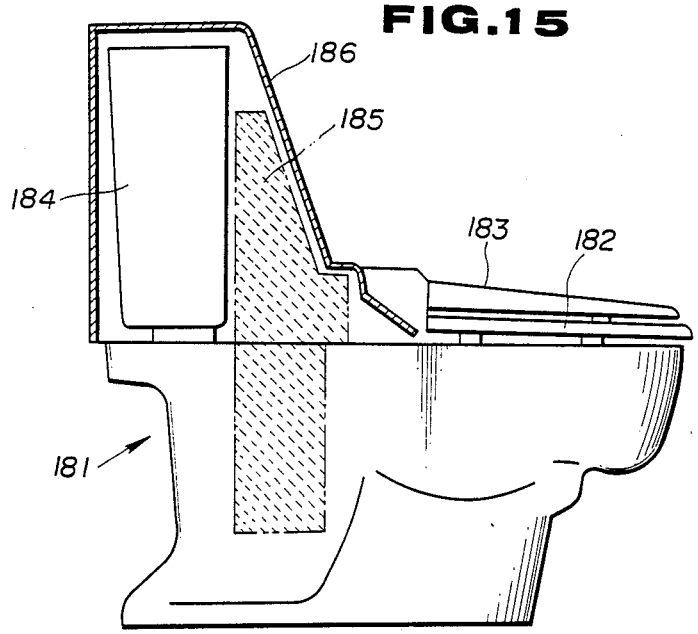
FIG. 15 is a side elevational view, partly in cross section, of a bowl, showing a urine analyzer location.

FIGS. 15 and 16 illustrate an embodiment directed to a toilet device having such a cover structure.

As shown in FIGS. 15 and 16, a seat 182 and a lid 183 are openably and closeably mounted on a front upper surface of a bowl 181, and a flushing water tank 184 for storing flushing water to wash the bowl 181 is mounted on a rear upper surface of the bowl 181. An urine analyzer 185 is disposed behind the flushing water tank 184 so that the urine analyzer 185 will not obstruct swinging movement of the seat 182 and the lid 183. The urine analyzer 185 and the flushing water tank 184 are entirely covered with a cover 186 which is placed from above the urine analyzer 185 and the flushing water tank 184.

Figure 17:
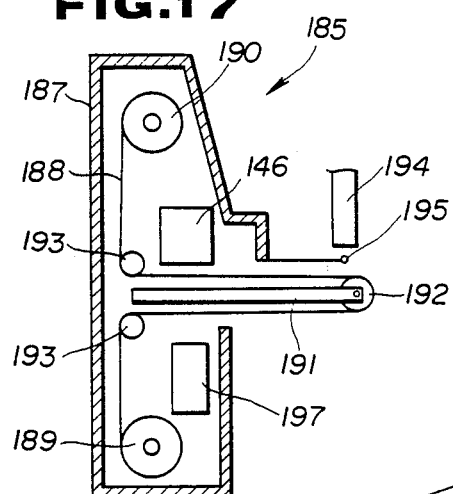
FIG. 17 is a view of a urine analyzer different from those of FIGS. 5 and 11.

As shown in FIG. 17, the urine analyzer 185 includes a housing 187 accommodating therein a supply roll 189 of a strip of test paper 188 and a takeup roll 190 for winding the used test paper 188, the supply and takeup rolls 189, 190 being vertically spaced from each other. An arm 191 disposed between the supply and takeup rolls 189, 190 projects forwardly out of the housing 187. A bend roll 192 is mounted on the projecting end of the arm 191. The strip of test paper 188 unreeled from the supply roll 189 is trained around guide rolls 193 and the bend roll 192 and wound around the takeup roll 190 which is intermittently rotated by a motor (not shown). A thermistor 195 attached to the housing 187 is disposed below a conduit 194 for supplying sampled urine as droplets onto the strip of test paper 188 between the upper guide roll 193 and the bend roll 192. The housing 187 also houses a sensor 196 comprising a photodiode and a control unit 197.

The control unit 197 applies a signal for feeding a predetermined length of test paper 188 to the motor coupled to the takeup roll 189. The control unit 197 also determines the amount of glucose, albumin, urobilin, or occult blood from the data items detected by the sensor 196, and displays the determined amount on a display unit.

Figure 18:
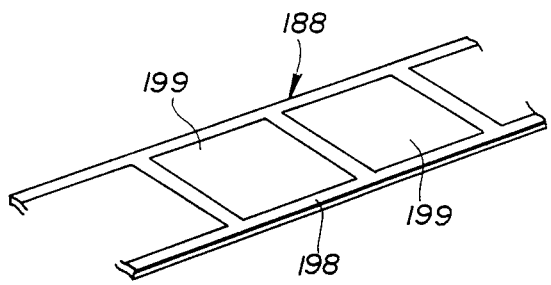
FIG. 18 is a fragmentary perspective view of a strip of test paper.

As shown in FIG. 18, the strip of test paper 188 comprises an elongate plastic film or sheet 197 and a plurality of test paper pads 199 attached to one surface of the plastic film 197 at spaced intervals.

Figure 19:
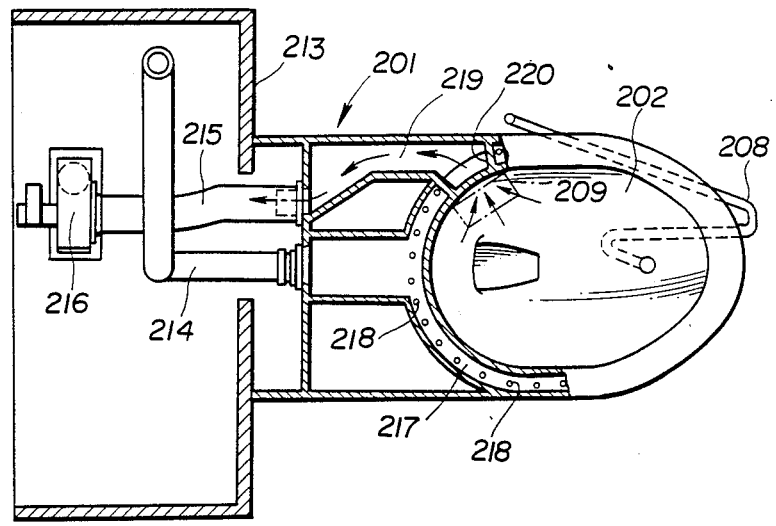
FIG. 19 is a plan view, partly in cross section, of a bowl having an air discharge unit near a urine analyzer.
Figure 20:
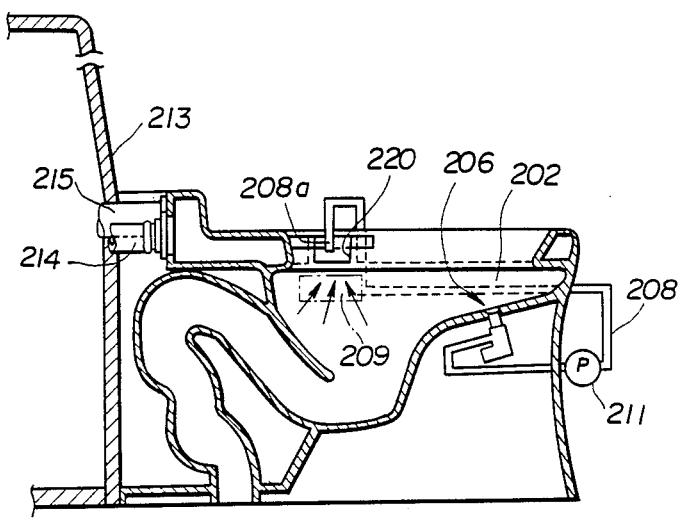
FIG. 20 is a vertical cross-sectional view of the bowl.

FIGS. 19 and 20 illustrate a toilet device in accordance with a still further embodiment of the present invention. In this embodiment, an air discharge opening or hole is disposed in the vicinity of a urine analyzer above a bowl. The air discharge opening can discharge out odor which is produced by urine when droplets of urine are applied from the end of the conduit to the urine analyzer.

More specifically, as shown in FIGS. 19 and 20, a box 213 is coupled to the rear portion of a bowl 201, and a pipe 214 joined to a flushing water tank and an air discharge pipe 215 are disposed in the box 213, the pipe 215 having an air discharge fan 216 therein. The bowl 201 has a bowl body 202 with its rim defining a passage 217 entirely therethrough which is connected to the pipe 214. The passage 217 has a plurality of spaced holes 218 defined in the bottom of the rim for supplying flushing water onto the inner bowl surface. An air discharge passage 219 is defined in one side of the bowl 201 at its upper rear portion, the air discharge passage 219 being connected to the air discharge pipe 215. The air discharge passage 219 defines a discharge air suction port 220 in an upper inner side surface of the bowl body 213 near a urine analyzer 209.

Excreted urine flows into a urine sampling area 206 of the bowl body 202 and then fed by a pump 211 via a conduit 208 to the urine analyzer 209.

While urine data items are being measured by the urine analyzer 209, the air discharge fan 216 is actuated to discharge air from around the urine analyzer 209 through the discharge air suction port 220, the air discharge passage 219, and the pipe 215, so that odor produced by the excreted urine will not be filled in the bathroom. The air discharge fan 216 may be continuously operated at all times, or may be turned on only when a user approaches a user sensor disposed near the bowl 201. Therefore, unwanted urine-induced odor can be discharged out not only while urine data items are being measured but also during normal usage of the toilet device. Alternatively, a urine passage sensor may be located near an open end 208a of the conduit 208, and the air discharge fan 216 may be turned on when urine is detected by the urine passage sensor, and may be subsequently turned off upon elapse of a predetermined period of time.

Figure 21:
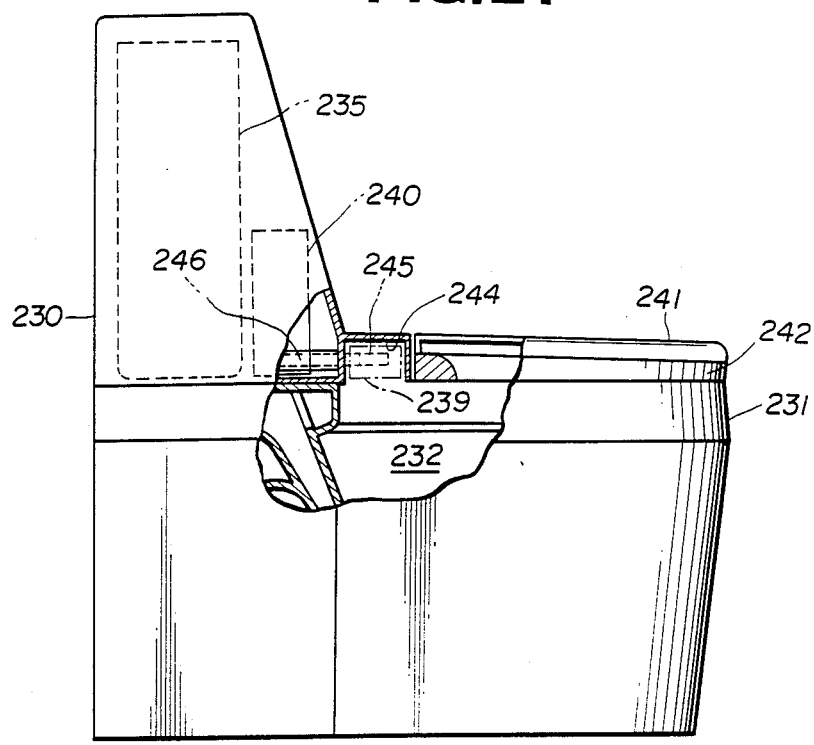
FIG. 21 is a side elevational view, partly in cross section, of a bowl different from that of FIG. 19.
Figure 22:
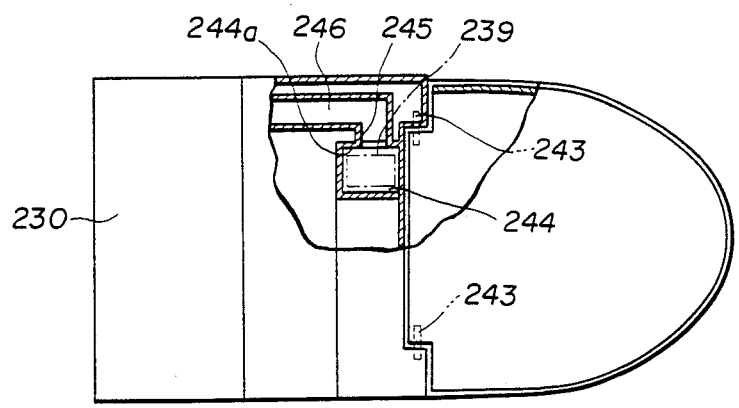
FIG. 22 is a plan view of the bowl illustrated in FIG. 21.

FIGS. 21 and 22 show another air discharge structure for use with a toilet device. A housing 230 covers a flushing water tank 235 for storing flushing water to wash a bowl body 232 of a bowl 231. The housing 230 also accommodates a urine analyzer 239 and a control unit 240 for processing analyzed data values and displaying them on a display unit. A seat 242 and a lid 241 are pivotally attached to a front end of the housing 230 through pivot shafts 243.

The urine analyzer 239 is disposed in a chamber 244 defined in a front portion of the housing 230. The chamber 244 has a side wall 244a having a discharge air suction port 245 communicating with an air discharge passage 246 leading to the exterior of the toilet device for discharging urine-induced odor while excreted urine is being analyzed.

FIGS. 23 through 27 show differently located urine analyzers according to other embodiments of the invention.

Figure 23:
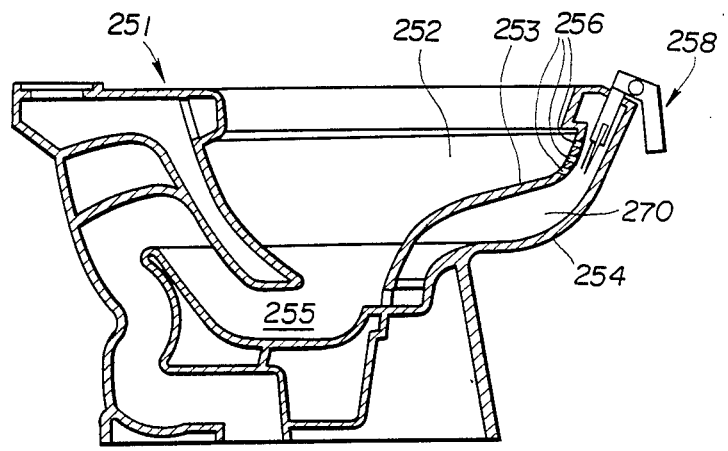
FIG. 23 is a vertical cross-sectional view of a bowl, showing a urine analyzer which is differently arranged and located from those of FIGS. 5, 11, and 17.
Figure 24:
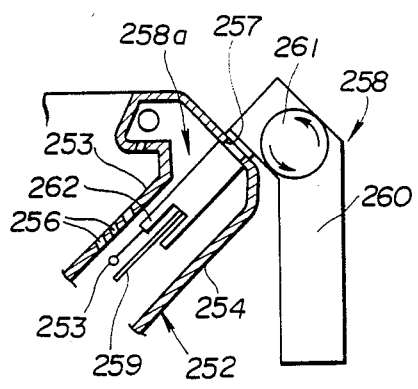
FIG. 24 is an enlarged fragmentary view of FIG. 23.

As shown in FIGS. 23 and 24, a bowl 251 includes a bowl body 252 of a hollow double-walled construction comprising an inner wall 253 and an outer wall 254 which define a space or enclosure 270 therebetween. The inner wall 253 has a plurality of urine sampling holes 256 defined in an urine receiving area 253a above a mass of water 255 contained or trapped in the bowl 251.

The outer wall 254 has an attachment hole 257 in which a urine analyzer 258 is mounted. As shown in FIG. 24, the urine analyzer 258 comprises a cassette 260 storing a number of pieces of test paper 259 and a reversible motor 261 for taking one of the test paper pieces 259 at a time from the cassette 260 and feeding the test paper piece 259 to a position below the urine sampling holes 256, the cassette 260 and the motor 261 being disposed outside of the enclosure 270 and the outer wall 254. The urine analyzer 258 includes a portion 258a disposed in the enclosure 270 and supporting a sensor 262 comprising a photodiode. A thermistor 263 projects forwardly from the sensor 262 for detecting droplets of urine.

Excreted urine which is discharged toward the bowl surface of the bowl body 252 flows down the inner wall 253 and drops through the urine sampling holes 256 into the enclosure 270. The droplets of urine are detected by the thermistor 263, which then energizes the motor 261 to feed one test paper piece 259 from the cassette 260 to the position below the urine sampling holes 256. The droplets of urine are now applied to the test paper piece 259 to cause a reagent contained in the test paper piece 259 to produce color. The motor 261 is reversed to move the test paper piece 259 back to the sensor 262, which detects the degree of coloration of the test paper piece 259. Based on the detected degree of coloration, a control unit determines the amount of glucose, albumin, urobilin, or occult blood in the urine, and displays the determined amount on a display unit.

After the urine examination is completed, the test paper piece 259 is discarded into the enclosure 270, and forced into the trap in the bowl 251 with flushing water.

Figure 25:
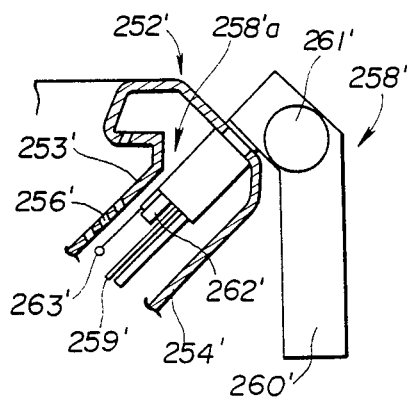
FIG. 25 is a view similar to FIG. 25, showing a modified urine analyzer.

According to an embodiment shown in FIG. 25, a sensor 262' is movable back and forth, and a piece of test paper 259' is not movable back. After droplets of urine have been detected by a thermistor 263', a test paper piece 259' is fed out below urine sampling holes 256'. Upon elapse of a preset period of time, thereafter, the sensor 262' is moved to a position above the test paper piece 259' for detecting the degree of coloration of the test paper piece 259'.

Figure 26:
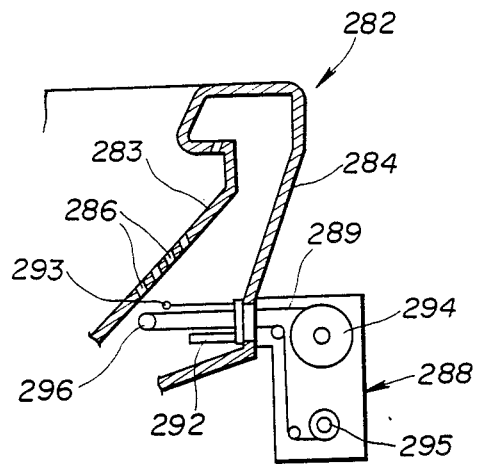
FIG. 26 is a view similar to FIG. 24, showing another urine analyzer.

FIG. 26 shows an embodiment in which a urine analyzer 288 disposed outside of an outer wall 284 of a bowl 282 accommodates a roll 294 of a strip of test paper 289 and a takeup roll 295 rotatable by a motor. Between an inner wall 283 and the outer wall 284, there is disposed a bend roll 296 disposed immediately near and below urine sampling holes 286 defined in the inner wall 283.

After droplets of urine from the urine sampling holes 286 have been detected by a thermistor 293, the takeup roll 295 is rotated to feed the test paper strip 289 from the roll 294 to a position below the urine sampling holes 286 to allow droplets of urine to be applied to the test paper strip 289. The degree of coloration of the test paper strip 289 is then detected by a sensor 292.

Figure 27:
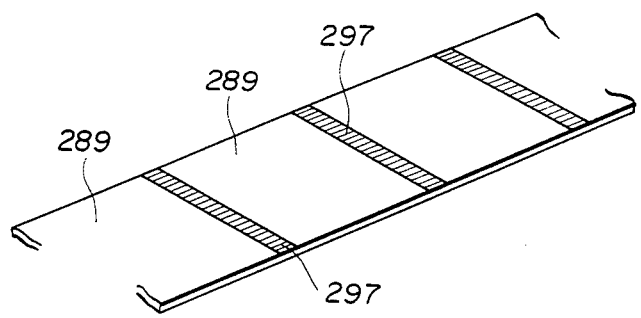
FIG. 27 is a perspective view of a strip of test paper different from that of FIG. 18.

The strip of test paper 289 is of a continuous narrow shape. As shown in FIG. 27, the strip of test paper 289 has a plurality of resin-impregnated webs 297 spaced at intervals in the longitudinal direction of the strip of test paper 289 so that no urine will permeate beyond areas defined by the webs 297 Rather than employing the webs 297, a plurality of spaced test paper pads may be attached to a resin sheet.

Although there have been described what are at present considered to be the preferred embodiments of the present invention, it will be understood that the invention may be embodied in other specific forms without departing from the spirit or essential characteristics thereof. The present embodiments are therefore to be considered in all aspects as illustrative, and not restrictive. The scope of the invention is indicated by the appended claims rather than by the foregoing description.

We claim:

1. A toilet device with a health examination system, comprising:
   a urine receiver;
   first measuring means for sampling a portion of urine from said urine receiver and measuring the proportion of a particular constituent of the urine;
   second measuring means for measuring at least one of the blood pressure, heart rate, and temperature of a user of said urine receiver; and
   display means for displaying the results of measurement by said first and second measuring means.

2. A toilet device according to claim 1, wherein said second measuring means includes means for measuring the blood pressure and heart rate, said means for measuring the blood pressure and heart rate being positioned for measuring the blood pressure and heart rate of the user while the user is using said urine receiver.

3. A toilet device according to claim 2, wherein said means for measuring the blood pressure and heart rate includes as looped band into which a finger of the user of said urine receiver can be inserted, said band comprising a tubular structure for receiving air, whereby the blood pressure and heart rate of the user can be measured through said band.

4. A toilet device according to claim 1, wherein said second measuring means includes means for measuring the temperature of the user, said means for measuring the temperature comprising a temperature sensor disposed in an area of said urine receiver to which urine excreted by the user is directly applied.

5. A toilet device according to claim 4, wherein said temperature sensor has an upper surface covered with a protective layer made of a thermal conductor and having a surface lying flush with a urine receiving surface of said urine receiver.

6. A toilet device according to claim 1, wherein said first measuring means comprises urine sampling means mounted on said urine receiver, a conduit having one end connected to said urine sampling means and extending therefrom, said conduit having an opposite end opening above a rear portion of an inner urine receiving surface of said urine receiver, and analyzing means for analyzing droplets of urine discharged from the open opposite end of said conduit.

7. A toilet device according to claim 6, wherein said urine sampling means comprises a hole defined in said inner urine receiving surface and valve means for selectively opening and closing said hole.

8. A toilet device according to claim 7, wherein said valve means comprises a valve seat fixedly supported in said hole, a urine passage defined in said valve seat, a valve body for selectively opening and closing said urine passage in coaction with said valve seat, and actuator means for actuating said valve body.

9. A toilet device according to claim 8, wherein said actuator means comprises a motor, a movable member movable back and forth by said motor, and a transmission member for transmitting movement of said movable member to said valve body.

10. A toilet device according to claim 8, wherein said valve means further includes a cap-shaped strainer covering said valve seat and said valve body.

11. A toilet device according to claim 8, wherein said valve means further includes communicating means providing communication between said urine passage and said one end of said conduit.

12. A toilet device according to claim 8 further comprising cassette means for storage of a plurality of test papers for receiving urine samples from said urine sampling means.

13. A toilet device as recited in claim 12 further comprising pump means in said conduit for providing said urine samples to said test papers.

14. A toilet device according to claim 6, wherein said first measuring means further includes washing means for washing the interior of said conduit, said washing means comprising a flushing water tank and a water supply pipe connected between said flushing water tank and a portion of said conduit.

15. A toilet device according to claim 14, wherein said flushing water tank comprises a tank for storing flushing water for washing said urine receiver.

16. A toilet device according to claim 6, wherein said first measuring means further includes removing means for removing urine scales within said conduit, said removing means comprising a cleanser tank and a cleanser supply pipe connected between said cleanser tank and a portion of said conduit.

17. A toilet device according to claim 6, wherein said urine receiver comprises an inner wall having said urine receiving surface and an outer wall disposed outwardly of said inner wall, said urine sampling means comprises a plurality of through holes defined in said urine receiving surface of said inner wall, a concave portion defined on said outer wall in confronting relation to said through holes, and a suction fitting mounted on a bottom of said concave portion and connected to said one end of said conduit.

18. A toilet device according to claim 6, wherein said urine sampling means comprises a pipe disposed in said urine receiver and extending forwardly from a rear portion of said urine receiver, and a urine suction unit disposed on a distal end of said pipe; said one end of said conduit being coupled to said urine suction unit, said conduit having a portion extending through said pipe.

19. A toilet device according to claim 18, wherein said pipe is movable back and forth in a longitudinal direction thereof.

20. A toilet device according to claim 18, wherein said pipe is angularly movable laterally of said urine receiver about a rear end of the pipe.

21. A toilet device according to claim 18 wherein said pipe is moveable for moving said urine suction unit relative to said urine receiver.

22. A toilet device according to claim 6, wherein said analyzing means is disposed rearwardly of said urine receiver in the vicinity of said opposite end of the conduit, said analyzing means comprising a plurality of pieces of test paper, a storage case storing said pieces of test paper and capable of feeding out said pieces of test paper, one at a time, laterally toward a position below the open opposite end of said conduit, and a photoelectric sensor for detecting the degree of coloration of a piece of test paper fed from said storage case when the droplets of urine are applied from the open opposite end of said conduit to said piece of test paper.

23. A toilet device according to claim 22, wherein said analyzing means further includes a urine passage sensor disposed on said conduit near said open opposite end thereof.

24. A toilet device according to claim 19, wherein each of said pieces of test paper comprises a resin sheet and a plurality of test paper pads attached to said resin sheet, said test paper pads being capable of producing colors by contact with different constituents of the urine.

25. A toilet device according to claim 22, wherein said analyzing means further includes a rack disposed directly below the open opposite end of said conduit for placing a piece of test paper thereon, a cylinder unit movable between said rack and said storage case, and a guide plate disposed between said rack and said storage case, said cylinder unit having a suction cup for attracting the lower surface of a lowermost piece of test paper in said storage case and drawing said lowermost piece of test paper from said storage case onto said guide plate, and a rod for pushing said piece of test paper along said guide plate onto said rack.

26. A toilet device according to claim 25, wherein said analyzing means further includes rack drying means disposed near said rack for applying heated air to said rack.

27. A toilet device according to claim 6, further including a flushing water tank disposed on a rear portion of said urine receiver for storing flushing water to wash said urine receiving surface, said analyzing means being disposed rearwardly of said urine receiver and forwardly of said flushing water tank, and a cover covering said analyzing means and said flushing water tank.

28. A toilet device according to claim 27, wherein said analyzing means includes a pair of vertically spaced upper and lower rolls, an arm disposed between said upper and lower rolls and extending laterally below the open opposite end of said conduit, a bend roll mounted on a distal end of said arm, a strip of test paper wound on said upper roll and extending along said arm and around said bend roller toward said lower roll, and a photoelectric sensor for detecting the degree of coloration of the strip of test paper between said upper roller and said bend roller when the droplets of urine are applied from the open opposite end of said conduit to said strip of test paper.

29. A toilet device according to claim 28 wherein said strip of test paper comprises an elongate sheet and a plurality of test paper pads attached to one surface of said elongate sheet, at spaced intervals from one another.

30. A toilet device according to claim 29 wherein said analyzing means includes control means for feeding a predetermined length of said strip of test papers and for determining component fractions of a plurality of items detected by said photoelectric sensor.

31. A toilet device according to claim 6, wherein said urine receiver has deodorizing means having a deodorizing opening near the open opposite end of said conduit.

32. A toilet device according to claim 31, wherein said deoderizing means includes an air discharge passage extending from said deoderizing opening to the exterior of the toilet device, and an air discharge fan disposed in said air discharge passage.

33. A toilet device according to claim 6, wherein said analyzing means is disposed rearwardly of said urine receiver in the vicinity of said opposite end of the conduit, said analyzing means comprising a piece of test paper, means for supporting said piece of test paper, and a photoelectric sensor for detecting the degree pf coloration of the piece of test paper when the droplets of urine are applied from the open opposite end of said conduit to said piece of test paper.

34. A toilet device according to claim 1, wherein said urine receiver comprises an inner wall having said urine receiving surface and an outer wall disposed outwardly of said inner wall, said first measuring means comprising urine sampling means comprising a plurality of through holes defined in said urine receiving surface of said inner wall, and analyzing means disposed between said inner and outer walls for analyzing droplets of urine discharged from said urine analyzing means.

35. A toilet device according to claim 34, wherein said analyzing means is disposed near said through holes, said analyzing means comprising a plurality of pieces of test paper, a storage case storing said pieces of test paper, feed means for feeding said pieces of test paper, one at a time, from said storage case to a position immediately near and below said through holes, and a photoelectric sensor for detecting the degree of coloration of the piece of test paper fed out of said storage case when the droplets of urine are applied from said through holes to said piece of test paper.

36. A toilet device according to claim 35, wherein said analyzing means further includes detecting means for detecting droplets of urine from said through holes, said detecting means being electrically connected to said feed means such that when droplets of urine are detected by said detecting means, said feed means feeds one piece of test paper at a time from said storage case to allow the droplets of urine to fall on said one piece of test paper.

37. A toilet device according to claim 34, wherein said analyzing means comprises a strip of test paper extending substantially horizontally immediately near and below said through holes, and a photoelectric sensor for detecting the degree of coloration of the strip of test paper when the droplets of urine are applied from said through holes to said piece of test paper, said strip of test paper having opposite ends engaging supply and takeup rolls, respectively, disposed outwardly of said outer wall.

38. A toilet device according to claim 37, wherein said strip of test paper includes webs extending transversely thereof and disposed at spaced intervals longitudinally thereof, said webs being impregnated with resin so that urine will not permeate into the webs.

39. A toilet device according to claim 37, wherein said strip of test paper comprises a resin sheet and a plurality of test paper pads attached to said resin sheet at spaced intervals longitudinally thereof.

* * * * *